US008376752B2

(12) United States Patent
McDevitt (10) Patent No.: US 8,376,752 B2
(45) Date of Patent: Feb. 19, 2013

(54) NASAL INSPIRATORY RESISTANCE TRAINER

(75) Inventor: Jason P. McDevitt, Williamsburg, VA (US)

(73) Assignee: College of William and Mary, Williamsburg, VA (US)

( * ) Notice: Subject to any disclaimer, the term of this patent is extended or adjusted under 35 U.S.C. 154(b) by 1043 days.

(21) Appl. No.: 12/371,154

(22) Filed: Feb. 13, 2009

(65) Prior Publication Data

US 2009/0205642 A1   Aug. 20, 2009

Related U.S. Application Data

(60) Provisional application No. 61/028,953, filed on Feb. 15, 2008, provisional application No. 61/040,169, filed on Mar. 28, 2008.

(51) Int. Cl.
*G09B 23/28* (2006.01)
(52) U.S. Cl. .................................................. 434/262
(58) Field of Classification Search .............. 434/262
See application file for complete search history.

(56) References Cited

U.S. PATENT DOCUMENTS

| 2,672,138 | A | * | 3/1954 | Carlock .................. 128/207.18 |
|---|---|---|---|---|
| 4,334,533 | A | * | 6/1982 | Henkin ................... 128/205.28 |
| 4,601,465 | A | * | 7/1986 | Roy ................................ 482/13 |
| 4,782,832 | A | * | 11/1988 | Trimble et al. .......... 128/207.18 |
| 5,558,089 | A | * | 9/1996 | Castiglione .............. 128/206.24 |
| 6,010,459 | A | * | 1/2000 | Silkoff et al. ................. 600/532 |
| 6,083,141 | A | * | 7/2000 | Hougen ......................... 482/13 |
| 6,158,432 | A | * | 12/2000 | Biondi et al. ............ 128/204.21 |
| 6,171,314 | B1 | | 1/2001 | Rotramel |
| 6,203,560 | B1 | * | 3/2001 | Blach et al. ................... 606/199 |
| 6,223,744 | B1 | * | 5/2001 | Garon ....................... 128/200.14 |
| 6,352,548 | B1 | * | 3/2002 | Blach et al. ................... 606/199 |
| 6,484,722 | B2 | * | 11/2002 | Bostock et al. .......... 128/206.19 |
| 6,510,846 | B1 | * | 1/2003 | O'Rourke ............... 128/200.21 |
| 6,513,526 | B2 | * | 2/2003 | Kwok et al. ............. 128/206.24 |
| 6,561,184 | B2 | | 5/2003 | Chiang |
| 6,581,598 | B1 | * | 6/2003 | Foran et al. ............. 128/204.23 |
| 6,615,834 | B2 | * | 9/2003 | Gradon et al. ........... 128/207.11 |
| 6,662,803 | B2 | * | 12/2003 | Gradon et al. ........... 128/205.25 |
| 6,669,649 | B2 | * | 12/2003 | Kahn ............................. 600/529 |
| 6,722,360 | B2 | * | 4/2004 | Doshi ...................... 128/200.24 |
| 6,776,162 | B2 | * | 8/2004 | Wood ....................... 128/207.18 |
| 6,848,446 | B2 | * | 2/2005 | Noble ...................... 128/207.18 |
| 7,036,508 | B2 | * | 5/2006 | Kwok ...................... 128/207.11 |
| 7,094,206 | B2 | * | 8/2006 | Hoffman ....................... 600/529 |
| 7,334,581 | B2 | * | 2/2008 | Doshi ...................... 128/207.14 |
| 7,406,965 | B2 | * | 8/2008 | Kwok et al. ............. 128/206.21 |
| 7,735,491 | B2 | * | 6/2010 | Doshi et al. ............. 128/207.18 |
| 7,735,492 | B2 | * | 6/2010 | Doshi et al. ............. 128/207.18 |
| 7,798,148 | B2 | * | 9/2010 | Doshi et al. ............. 128/207.18 |
| 7,856,979 | B2 | * | 12/2010 | Doshi et al. ............. 128/206.11 |
| 7,905,232 | B2 | * | 3/2011 | Olsen et al. ............. 128/207.18 |
| 7,992,564 | B2 | * | 8/2011 | Doshi et al. ............. 128/207.18 |
| 8,136,527 | B2 | * | 3/2012 | Wondka ................... 128/207.18 |
| 8,182,505 | B2 | * | 5/2012 | Blach et al. ................... 606/199 |

(Continued)

OTHER PUBLICATIONS http://www.google.com/?tbm=pts.*

(Continued)

*Primary Examiner* — Kurt Fernstrom
*Assistant Examiner* — Dolores Collins
(74) *Attorney, Agent, or Firm* — Jason P. McDevitt (57) ABSTRACT

Devices and methods useful for enhancing respiration quality in humans are described herein. In particular, the present invention relates to devices and methods useful for the treatment, prevention, and/or management of respiratory disorders and associated complications. Herein, a training device is described that increases the difficulty of nasal breathing.

3 Claims, 3 Drawing Sheets

U.S. PATENT DOCUMENTS

| | | |
|---|---|---|
| 8,215,308 B2 * | 7/2012 | Doshi et al. ............... 128/207.18 |
| 2004/0255939 A1 | 12/2004 | Feldman |
| 2007/0191688 A1 * | 8/2007 | Lynn .............................. 600/300 |
| 2008/0035147 A1 | 2/2008 | Kirby et al. |
| 2012/0052469 A1 * | 3/2012 | Sobel et al. ................... 434/262 |

OTHER PUBLICATIONS

Cooper et al., "Effect of two breathing exercises (Buteyko and pranayama) in asthma: a randomized controlled trial", Thorax, (2003), vol. 58, pp. 674-679.

Cowie et al., "A randomized controlled trial of the Buteyko technique as an adjunct to conventional management of asthma", Respiratory Medicine (2008), vol. 102, pp. 726-732.

Bishop et al., "The use of mouth taping in people with asthma: a pilot study examining the effects on end-tidal carbon dioxide levels", Physiotherapy (2007), vol. 93, pp. 129-136.

Grossman et al., "Breathing-control lowers blood pressure", Journal of Human Hypertension (2001), vol. 15, pp. 263-269.

Elliott et al., "Hypertensive Outpatients Associated With Use of a Device to Assist With Slow Breathing", The Journal of Clinical Hypertension (2004), vol. 6, pp. 553-561.

* cited by examiner

NASAL INSPIRATORY RESISTANCE TRAINER

CROSS-REFERENCE TO RELATED APPLICATIONS

This application claims the benefit of and priority to U.S. Provisional Patent Application Ser. No. 61/028,953, filed Feb. 15, 2008, and further claims the benefit of and priority to U.S. Provisional Patent Application Ser. No. 61/040,169, filed Mar. 28, 2008, the entire disclosures of which are incorporated by reference herein.

STATEMENT REGARDING FEDERALLY SPONSORED RESEARCH OR DEVELOPMENT

Not applicable

FIELD OF INVENTION

The present invention relates to devices and methods useful for enhancing breathing quality in humans and for treating respiratory disorders such as asthma and rhinitis.

BACKGROUND

Over the years, a variety of nasal dilators, nose braces, nasal strips, bandages, breathing equipment, jaw retainers, orthodontic inserts, tongue retainers, mechanisms, instruments and other devices have been suggested to improve breathing quality and have met with varying degrees of success. Devices that require insertion into the nostrils have been tried, with the intent of opening the nostrils and allow more air to enter the nose. Various nasal strips have also been suggested. In one version of the Breathe Right® nasal strip manufactured by CNS, Inc. of Minneapolis, Minn., adhesive strips are lined with two parallel plastic rods. When placed across the bridge of the nose, an adhesive nasal strip adheres to the soft area above the flare of each nostril and provides an excessive pulling force to lift and open the nasal passages. In another version of the Breathe Right® nasal strip, a flexible metal strip is attached to an adhesive band that is placed on the inside of the nose. The spring action of the metal strip pulls the sides of the nose outward. Many other devices have been proposed with the intent of increasing air flow through the nose.

Another approach, analogous to resistance weight training, or high-altitude training, is to practice breathing through artificially high resistance, thereby potentially increasing the strength of various muscles involved in breathing. In other words, rather than making breathing easier by increasing air flow through the nose, this approach makes breathing more difficult during training sessions, hopefully making breathing easier during normal conditions. There are numerous inspiratory resistance trainers that are currently marketed, but these devices require oral inhalation by users. Such devices may indeed increase the strength of various muscles involved in breathing, as advertised, but oral inhalation is generally disfavored by the medical community, and these devices may train users to revert to oral breathing when breathing is difficult, which can be deleterious for users.

Asthma is a chronic respiratory disease afflicting an increasingly large number of individuals. There is no known cure, and treatments are aimed at controlling symptoms and complications. While pharmacotherapy is widely used to treat asthma, many patients seek additional or alternative non-pharmaceutical therapies.

One such therapy utilizes the so-called Buteyko breathing technique. Asthma is often correlated with frequent hyperventilation and low levels of carbon dioxide in the bloodstream. High carbon dioxide levels act on the airway smooth muscle tissue to cause bronchodilation. Proponents of the Buteyko approach believe that asthma can be effectively managed by breathing reduced air volumes. This practice will increase the carbon dioxide level in the bloodstream, purportedly leading to an increase in the body's carbon dioxide setpoint, and therefore allowing higher levels of carbon dioxide to accumulate in the body before initiation of respiration.

In U.S. Patent Application No. 20040255939, Feldman describes a method of increasing the carbon dioxide level in a patient by administering to the patient an inhalant that comprises a mixture of carbon dioxide and atmospheric air. The method can be used to treat a patient suffering from asthma, allergies, muscle tension, pain, insomnia, and/or mental stress, and is described as being faster than the Buteyko breathing technique.

Nasal breathing, particularly nasal inhalation, is widely believed to be preferred to oral breathing, particularly for asthmatics, as nasal inhalation humidifies, warms, and filters incoming air. Bishop et al. (*Physiotherapy* 93 (2007) 129-136) have recently demonstrated that forced nasal breathing, via mouth taping, has the effect of increasing end-tidal carbon dioxide levels.

Scientific evidence has shown that paced breathing can lower blood pressure significantly by relaxing the muscles surrounding constricted blood vessels. The problem for many people, however, is that proper paced breathing requires years of training and individualized coaching. Typically, it requires some effort to consciously reduce breathing rate. A tonal-based biofeedback system has been incorporated into a portable electronic device (RESPeRATE®, produced by InterCure, Inc.) to lower blood pressure naturally by using biofeedback tones to direct breathing and reduce breathing rate. This FDA-approved device has been clinically demonstrated to reduce blood pressure. It also requires the user to wear a chest strap that monitors breathing, and retails for several hundred dollars.

BRIEF SUMMARY OF THE INVENTION

The present invention relates to devices and methods useful for enhancing respiration quality in humans. The present invention relates to devices and methods useful for the treatment, prevention, and/or management of respiratory disorders and associated complications. The present invention further relates to devices and methods useful for reducing blood pressure.

Herein, a training device is described that increases the difficulty of nasal breathing. The methods comprise inhaling air through the nose while using a device that increases the difficulty of nasal breathing. The device is a nasal inspiratory muscle trainer ("NIRT") that is designed for nasal inhalation, rather than oral inhalation as in prior art inspiratory breathing devices. A subject utilizing the devices and methods of the invention can experience one or more of the following: increased tolerance for carbon dioxide in the body, reduced respiration rate, reduced breathing volume, enhanced nasal/oral breathing ratio, strengthened breathing muscles, and reduced blood pressure.

An asthmatic subject utilizing a NIRT device according to the methods of the invention is exposed to conditions of impaired air flow somewhat analogous to asthma attacks, and therefore can hone techniques useful in dealing with real asthma attacks, including: avoiding panic, reducing respiratory volume, and breathing through the nose in spite of increased air resistance. Furthermore, the methods of the invention help to prevent asthma attacks by decreasing habitual hyperventilation and increasing the proportion of inhalations through the nose relative to inhalations through the mouth.

NIRT Devices of the present invention include devices useful for restricting air flow through the nose. In some embodiments of the invention, the devices can restrict air flow into the nose with minimal or even non-existent physical contact with the nose. Alternatively, devices of the present invention can attach to the exterior surface of the nose, or can be inserted into or attach to interior surfaces of the nose. For example, in one embodiment, the device is a nose mask that reduces air flow into the nose. In another embodiment, the device is a disposable plug that is inserted into one or both nostrils. In another embodiment, the device attaches to the exterior surface of the nose and exerts a compressive pressure that pushes the nostrils towards a closed position, thereby decreasing the cross-sectional area through which inhaled air and exhaled air can travel.

In some embodiments, the NIRT device is a nose clip. Unlike prior art nose clips useful for swimming and diving, NIRT devices of the present invention are not intended to prevent nasal breathing, but rather to encourage and develop nasal breathing in spite of resistance. The compressive force of the nose clip can be generated, for example, by spring mechanisms, restoration forces following a shape distortion, or any other methods known in the art. Ideally, the nose clip is not uncomfortable during use. In some embodiments, the extent of available cross-sectional area in the nasal passage through which air can flow is controlled by moderating the compressive pressure of the device. In some embodiments, said cross-sectional area is controlled by the placement of the device. In some embodiments, the device includes sensors to monitor air flow into and/or out of the nose and/or mouth. In some embodiments, sensors are used to measure respiratory rate, or induce changes in respiratory rate. In some embodiments, sensors are included to monitor diaphragmatic breathing. In some embodiments, sensors are used in conjunction with the device to measure carbon dioxide concentration in the blood and/or exhaled air. In some embodiments, attachments are included to provide a physical impediment that reduces or prevents oral breathing.

In preferred embodiments of the invention, the device of the present invention is used by a subject for between about five minutes and two hours at least one time per month, preferably used for between abut five minutes and one hour at least one time per week, and more preferably used multiple times per week for a duration of five minutes or more.

The present invention is useful for the treatment, management, and prevention of symptoms relating to asthma and rhinitis. For example, the methods and devices of the present invention can be used on subjects with allergies to allergens such as ragweed or tree pollen, ideally training subjects to avoid hyperventilating when airflow is impaired by allergy-induced congestion.

The present invention is also useful for reducing blood pressure. Individuals using a NIRT device of the present invention typically breathe more slowly when using the device than they do when not wearing the device. In most cases, this reduced breathing rate is not the result of a conscious decision to breathe more slowly, but instead is a natural result of the increased inhalation and exhalation times required to process a normal volume of air. The NIRT-induced reduction in breathing rate can induce a relaxation of constricted blood vessels, prompting a reduction in blood pressure.

DETAILED DESCRIPTION OF THE INVENTION

The present invention is directed to methods and devices for enhancing respiration quality in humans. The methods comprise training via nasal inhalation while using a device that increases the difficulty of nasal breathing, thereby producing a conditioning effect that improves breathing.

As used herein, each of the following terms has the meaning associated with it as described below.

As used herein, a subject with "improved breathing" has one or more of the following results:
(a) increased baseline concentrations of carbon dioxide in the alveoli (provided the subject started with a baseline concentration of less than 6% carbon dioxide in the alveoli), as measured by increases in carbon dioxide content in exhaled air (end-tidal carbon dioxide);
(b) reduced respiration rate, as evidenced by a reduction in the average number of breaths taken per minute;
(c) enhanced nasal/oral breathing ratio, as evidenced by an increased in the percentage of nasal inspiration (breathing in through the nose) relative to oral inspiration (breathing in through the mouth);
(d) enhanced diaphragmatic breathing ratio, as evidenced by an increase in the percentage of diaphragmatic breathing relative to thoracic breathing;
(e) reduced breathing volume per unit time, reflected in a decrease in the volume of air breathed per minute, provided the subject started with an abnormally high average breathing volume per unit time; and
(f) increased strength and/or endurance in the inspiratory breathing muscles.

As used herein, "diaphragmatic breathing" means breathing deeply into the lungs by flexing the diaphragm. This type of breathing is marked by expansion of the abdominal region, rather than the chest region, upon inhalation. In thoracic breathing, the cross-sectional abdominal diameter often decreases or stays the same during inhalation and/or increases during exhalation. In the scientific literature, this is sometimes referred to as paradoxical breathing, reverse breathing, or upper thoracic breathing. Typically, breathing is not entirely diaphragmatic or entirely thoracic, but some combination of the two, and varies greatly even within a single subject. "Diaphragmatic breathing ratio" is the ratio of diaphragmatic breathing to thoracic breathing.

As used herein, a "nasal inspiratory resistance trainer" ("NIRT") is a device, applied to the outside or inside of the nose, that increases the difficulty of nasal breathing, and is used by subjects during breathing exercises wherein the subject's breathing is (intentionally) predominantly nasal inspiration.

As used herein, the "$CO_2$ setpoint" refers to the average baseline concentration of carbon dioxide in the blood of a subject over a 24-hour period. The concentration of carbon dioxide in the blood can vary based on a number of different factors, e.g., time of day, diet, exertion level, stress, and body temperature. Calculating the $CO_2$ setpoint requires obtaining concentrations of carbon dioxide in the blood at a number of different time points, and averaging them. In asthmatic subjects, it can be desirable to increase the $CO_2$ setpoint.

In preferred embodiments, the nasal inspiratory resistance trainer does not cause significant discomfort when it is used by subjects. In one embodiment, the NIRT is a nose clip. In such embodiments, it is preferable that the NIRT increases the inspiratory resistance associated with nasal breathing. In preferred embodiments, the initial air flow volume per exhalation is reduced during use by between about 5% and about 75% relative to the initial air flow volume per exhalation when the device is not being used. As used herein, the "initial air flow volume per exhalation" refers to the average volume of air flow through the nose during the first second of exhalation.

The present invention is particularly useful for the treatment, management, and prevention of symptoms relating to respiratory disorders such as asthma and rhinitis. The methods of the present invention are useful for the treatment of both allergic asthma and non-atopic asthma, and are useful for the treatment of allergic rhinitis and non-allergic rhinitis. For example, the methods and devices of the present invention are useful in training a child suffering from seasonal allergic rhinitis (e.g., "hay fever") to avoid overbreathing and to better cope with nasal congestion. There is a tendency in many individuals with asthma or rhinitis to inhale more air than is needed, which can decrease carbon dioxide levels in the blood, which can lead to increased mucus production, thereby exacerbating congestion and often increasing the tendency to hyperventilate. The methods and devices of the present invention assist in disrupting this cycle.

The methods and devices of the present invention may be useful for reducing blood pressure. This outcome is particularly relevant for individuals having hypertension or prehypertension, and may be most effective when used by individuals who typically have high respiration rates. That said, the methods and devices of the invention may also be useful for individuals not afflicted with hypertension or prehypertension, particularly when used on a preventative basis. Individuals with prehypertension have a systolic pressure (top number) ranging from 120 to 139 millimeters of mercury (mm Hg) or a diastolic pressure (bottom number) ranging from 80 to 89 mm Hg. Individuals with hypertension have a systolic pressure greater than 140 mm Hg or a diastolic pressure greater than 90 mm Hg.

In one embodiment of the invention, subjects having hypertension or prehypertension train with the NIRT device three or more times per week, for at least ten minutes per session. Subjects training with the device may experience reduced blood pressure relative to what the blood pressure would otherwise be in the absence of training with the device. To date, such training has only been performed on individuals having normal blood pressure, and clinical trials are planned to investigate the extent of blood pressure reduction that can be achieved by training with NIRT devices.

The methods and devices of the present invention are compatible with other methods for reducing blood pressure, including exercise, use of other medical devices to reduce blood pressure, and pharmacotherapy such as administration of angiotensin-converting enzyme inhibitors, angiotensin II receptor blockers, beta blockers, and calcium channel blockers.

The devices of the present invention may also be useful for athletic training, or for reducing snoring in a subject if sufficient training with the device reduces the tendency of a subject to inhale orally during sleep.

Use and Positioning of NIRT Devices

The positioning of devices of the present invention during use can vary. In preferred embodiments, devices of the present invention are constructed such that consistent placement on, around, or within the nose can be facilitated, thereby allowing more consistent resistance between different training sessions. In some embodiments of the invention, the NIRT is a nose clip having markings or gradations that facilitate consistent placement on the nose.

When the NIRT is a nose clip, the nose clip is normally applied to the outside of the nose, and kept in place via a compressive force that squeezes the nose. Obviously, a nose clip can be placed onto a nose at a variety of positions (e.g., vertical displacements relative to the bridge of the nose, horizontal displacement relative to the tip of the nose), and nose clips of the present invention can have widely varying dimensions. In some embodiments of the invention, a nose clip is applied near the tip of the nose, particularly when the nose clip is a nose clip having sufficient compressive force that it can also be used during swimming to prevent nasal inspiration (i.e., a "high compressive force nose clip"). High compressive force nose clips can make nasal breathing overly difficult if positioned, for example, closer to the alar-facial groove and away from the tip of the nose. In other embodiments of the invention, the nose clip can be worn conveniently and comfortably at any position on the nose that restricts air flow significantly, but does not restrict air flow so much that subjects cannot use the device without having to resort to oral inhalation.

Nose clips are disclosed, for example, in U.S. Pat. Nos. 4,231,360 and 5,103,813. U.S. Pat. No. 6,561,184 discloses nose clips and includes a discussion of prior art nose clips, any of which could be used in accordance with the methods of the present invention. It is believed that all commercially available nose clips used for swimming, diving, and kayaking could also be used according to the methods of the present invention, although there are advantages, particularly with respect to user comfort, in using nose clips that are not high compressive force nose clips.

In some embodiments, the NIRT is a nose clip having a means for adjusting tension such that the force applied to the nostrils can be adjusted. In some embodiments, NIRT nose clip devices of the present invention have reduced compressive force relative to high compressive force nose clips that are useful for water sports (and that are thus intended to securely close the nostrils). In some embodiments of the invention, nose clips contain implements that distribute the force applied to the nose over a greater area, potentially reducing the discomfort. In some embodiments, the components of the nose clip that come into contact with the nose are soft, malleable, pads. In some embodiments of the present invention, the nose clips exert a compression force of less than 1 pound when the contact points are 2.0 cm apart. In some embodiments of the invention, the nose clips exert a compression force of less than 0.5 pounds when the contact points are 1.5 cm apart. In some embodiments of the invention, the nose clips exert a compression force of less than 0.3 pounds when the contact points are 1.5 cm apart.

In some embodiments of the invention, the compressive force applied by the nose clip does not differ substantially as a function of the distance between the contact points upon application to the nose. In other words, in these embodiments, the compression force experienced by a subject applying the device to a wide portion of his or her nose is not substantially higher than the compression force experienced when the device is applied to a narrow region of the nose (or to a more narrow nose). In these embodiments, the pressure applied when the contact points of the NIRT are relatively far apart is relatively close to the pressure applied when the contact points of the NIRT are reasonably close together. For example, in some embodiments of the invention, the compressive pressure applied by the nasal inspiratory resistance trainer when the contact points are 1.0 inches apart is less than 75% greater than the pressure applied by the nasal inspiratory resistance trainer when the contact points are 0.5 inches apart. Such embodiments facilitate production of a device that comfortably fits a large range of nose sizes.

Contact points in commercially available nose clips are frequently soft pads such as silicone or rubber pads. However, any material that facilitates comfort (e.g., elastic materials used in cushioning applications) can be used as contact points in nose clips of the present invention. Compressible foams, gels, and rubbers, including synthetic rubbers, are all suitable materials for use in nose clips as contact points or as components of contact points. Suitable thermoplastic foams include but are not limited to low density polyethylene ("LDPE") foams, natural rubber-cassava starch foams, and polyurethanes such as flexible polyether(urethane-urea) ("PEUU") foams. When viscoelastic gels are used to provide cushioning in the contact points, the gel can be covered with an elastic fabric such as spandex fabric, meaning that the spandex fabric would actually contact the skin of the nose.

In certain embodiments, the NIRT can include an attachment that makes oral inhalation difficult, or the NIRT can be combined with other devices that impair oral inhalation. For example, the NIRT can be used in conjunction with medical tape used to tape closed the mouth of a subject. In another embodiment, the NIRT can be used with a chin strap that makes it difficult for a subject to open his or her mouth.

When the NIRT is an intranasal obstructive device, the device is inserted into a subject's nostrils. In some embodiments, the intranasal obstructive device is constructed such that consistent placement in a subject's nose can be facilitated. For example, the intranasal obstructive device may have visible markings that facilitate placement at a certain depth.

Intranasal obstructive devices are disclosed e.g. in U.S. Pat. Nos. 3,457,917; 3,905,335; 4,052,983; 5,417,205; 5,568,808; and 5,890,491. Many of these devices can be used according to the methods of the invention, but have not previously been suggested for this use. Intranasal obstructive devices have some disadvantages relative to nose clips when used according to the methods of the invention, as their disposable nature may result in increased long-term costs for a user, as well as increased waste. Furthermore, they may be perceived as less comfortable, and less hygienic.

The duration and frequency of training sessions using the NIRT devices of the present invention can vary according to the methods of the invention. For example, the NIRT can be applied daily, or can be used sporadically. It can be applied for a short time, or can be utilized for multiple hours. In preferred embodiments, the NIRT is applied to the nose and utilized for at least five minutes at least one time per week.

Exemplary NIRT devices that are commercially available and can be used according to the methods of the present invention include, e.g., the Speedo Rubber Nose Clip, the Speedo Competition Nose Clip (both available from Speedo International Ltd., Nottingham, England), both of which are made out of rubber and stainless steel; and the Tyr Soft Pad Nose Clip, which is made of pliable soft polycarbonate with silicone pads, and is available from Tyr Sport, Inc., in Huntington Beach, Calif. Similar designs from other manufacturers are widely available.

Figure 1:
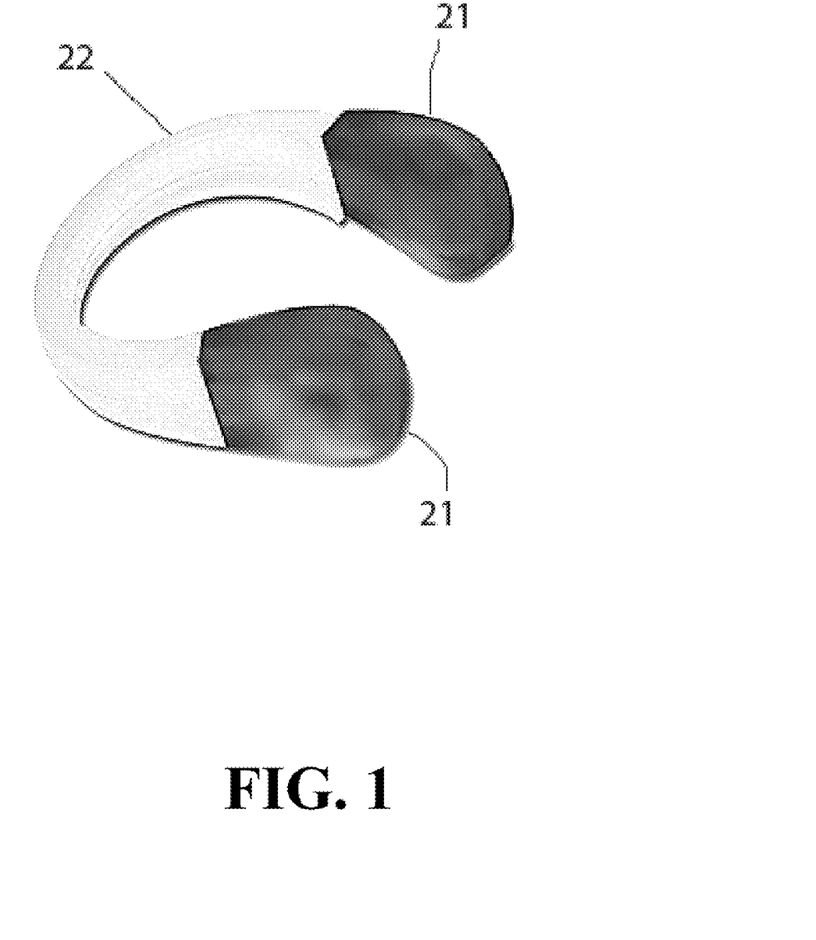
FIG. 1 is a schematic top view of a nose clip-style NIRT device.
Figure 2:
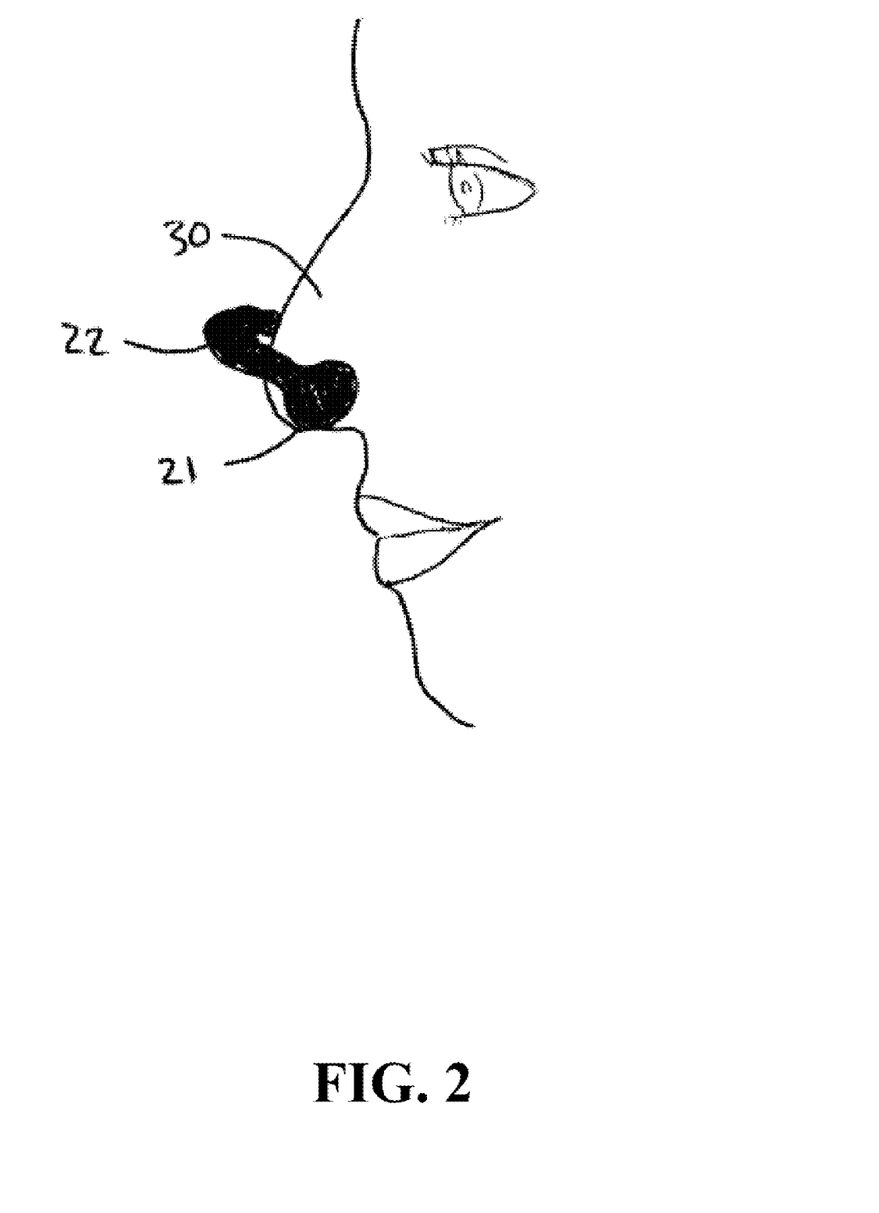
FIG. 2 is a side view of a human nose to which a NIRT device has been applied.
Figure 3:
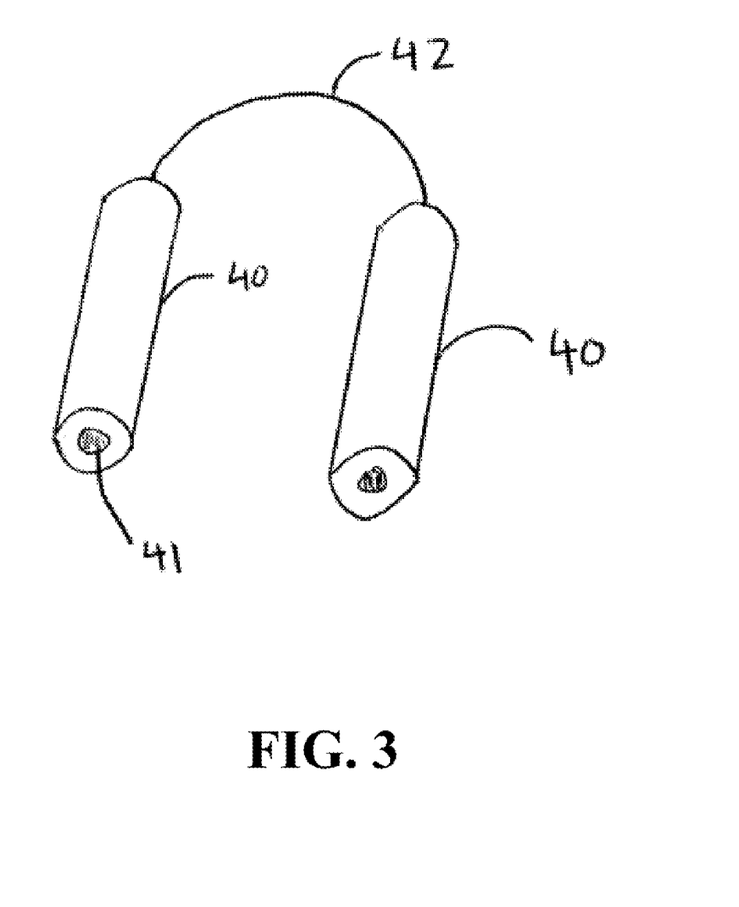
FIG. 3 is a front view of a NIRT device that is applied inside the nasal cavity when used according to the methods of the invention.

FIG. 1 is a schematic top view of a nose clip. End tips 21, which serve as contact points with the nose, are adjoined to a flexible U-shaped base 22, which typically is metal or plastic or rubber, or coated materials thereof. The device is applied to a subject's nose such that the deformable end tips 21 contact either side of a subject's nose 30, as pictured in FIG. 2. In FIG. 3, a NIRT device of the type that is inserted into the nasal cavity is shown, comprising compressible foam inserts 40, optionally including internal cavity 41 to facilitate air flow, and connected by connector 42.

The methods and devices of the present invention can be utilized by human subjects of any age, provided that the subject understands and can carry out the instruction to attempt to avoid oral breathing while the NIRT is applied.

EXAMPLES

The examples that follow are intended in no way to limit the scope of this invention but are provided to illustrate the methods of the present invention. Many other embodiments of this invention will be apparent to one skilled in the art.

Example 1

A commercially available adjustable nose clip (Speedo Rubber Nose Clip, available from Speedo International Ltd., Nottingham, England), of the type typically utilized while swimming, was used, without any modifications, as the NIRT device in this example. End-tidal carbon dioxide concentration and respiration rate were monitored using a BCI Capnocheck II Hand-held Capnograph.

Methods: Subjects were seated in a comfortable chair and directed to watch television. The nasal cannula of the sidestream capnograph was taped to the subject's face, and readings were commenced. The capnograph displayed the end tidal carbon dioxide and respiration rate, and the displayed values were recorded at 15 second intervals. After eight minutes, the NIRT was applied to the subject's face, and measurements were again recorded for eight additional minutes, at which time the NIRT was removed, and measurements were again recorded for eight more minutes.

Results: A pediatric subject (Subject 1), afflicted with asthma but asymptomatic at the time of the experiment, was monitored according to the method described above. Additionally, a non-asthmatic pediatric subject (Subject 2) and two non-asthmatic adults (Subjects 3 and 4) were also tested. Results are shown in Table 1 below, wherein "etCO2" is the average end-tidal carbon dioxide concentration (measured in mm Hg), and "RRPM" is the average calculated respiration rate per minute. On average, during periods when the NIRT device was applied, end-tidal carbon dioxide concentrations increased and RRPM decreased.

TABLE 1

| Conditions | Subject 1 | | Subject 2 | | Subject 3 | | Subject 4 | |
|---|---|---|---|---|---|---|---|---|
| | etCO2 | RRPM | etCO2 | RRPM | etCO2 | RRPM | etCO2 | RRPM |
| 0-8 minutes, no NIRT | 40.5 | 14.5 | 41 | 21.5 | 37 | 10 | 40 | 10.5 |
| 8-16 minutes, NIRT applied | 42 | 12 | 41 | 23 | 41 | 9 | 39 | 10 |

TABLE 1-continued

| Conditions | Subject 1 etCO2 | RRPM | Subject 2 etCO2 | RRPM | Subject 3 etCO2 | RRPM | Subject 4 etCO2 | RRPM |
|---|---|---|---|---|---|---|---|---|
| 16-24 minutes, no NIRT | 40.5 | 18 | 38.5 | 23.5 | 40 | 10 | 37 | 12 |

Example 2

A commercially available adjustable nose clip (Speedo Rubber Nose Clip, available from Speedo International Ltd., Nottingham, England) was used, without any modifications, as the NIRT device in this example. End-tidal carbon dioxide concentration and respiration rate were monitored using a BCI Capnocheck II Hand-held Capnograph. A commercially available breathing rate biofeedback device (RESPeRATE®, available from Intercure, Inc., New York, N.Y.) was also used, and affixed to the subject prior to commencement of the experiment.

The subject, a pediatric subject afflicted with asthma but asymptomatic at the time of the experiment, was seated in a comfortable chair and instructed to read. The tension bands used to monitor respiration in the RESPeRATE unit were applied to the subject. The nasal cannula of the sidestream capnograph was taped to the subject's face, and readings were commenced. End tidal $CO_2$ values were recorded at 15 second intervals. After four minutes, during which time the average end tidal CO2 value was 39.5 mm Hg, the RESPeRATE unit was turned on, headphones were placed on the subject's ears, and the RESPeRATE device was used according to its standard procedure, which is to relay biofeedback tones through the headphones to attempt to lower and then maintain the respiration rate below ten breaths per minute. End tidal $CO_2$ was again recorded at 15 second intervals for four additional minutes, during which time the average end tidal $CO_2$ reading increased to 44 mm Hg. The NIRT was then applied to the subject, while continuing to use the RESPeRATE device, and end tidal $CO_2$ was again recorded at 15 second intervals for eight additional minutes, during which time the average end tidal $CO_2$ reading was 46 mm Hg. Subsequently, the NIRT was removed, the RESPeRATE was turned off and the headphones were removed, and end tidal $CO_2$ was again recorded at 15 second intervals for a final four minutes, during which time the average end tidal $CO_2$ measurement dropped to 41 mm Hg.

The results indicate that utilization of the RESPeRATE device increased end tidal $CO_2$, and combining the RESPeRATE device and the NIRT further increased end tidal $CO_2$.

Example 3

A commercially available adjustable nose clip (Speedo Rubber Nose Clip, available from Speedo International Ltd., Nottingham, England), of the type typically utilized while swimming, was used, without any modifications, as the NIRT device in this example. End-tidal carbon dioxide concentration and respiration rate were monitored using a BCI Capnocheck II Hand-held Capnograph.

Methods: Subjects were seated in a comfortable chair and directed to watch television. The nasal cannula of the sidestream capnograph was inserted into the subject's nostrils, and the tubing was wrapped around the ears to keep the cannula in place. The capnograph displayed the end tidal carbon dioxide and respiration rate, and, after a two-minute acclimation period, the displayed values were recorded at 20 second intervals. After four minutes of recording the values, the NIRT device was applied to the subject's nose, and measurements were recorded for ten additional minutes, at which time the NIRT was removed, and measurements were recorded in the absence of the NIRT for four more minutes.

Results: A pediatric subject, afflicted with asthma but asymptomatic at the time of the experiment (although suffering from a cold), was monitored according to the method described above. Additionally, a non-asthmatic adult subject was also tested. Results are shown in Table 2, wherein "etCO2" is the average end-tidal carbon dioxide concentration (measured in mm Hg), and "RRPM" is the average calculated respiration rate per minute. On average, during periods when the NIRT device was applied, end-tidal carbon dioxide concentrations increased and RRPM decreased.

TABLE 2

| Conditions | Pediatric Subject etCO2 | RRPM | Adult Subject etCO2 | RRPM |
|---|---|---|---|---|
| 0-4 minutes, no NIRT | 43.2 | 12.0 | 44.7 | 10.3 |
| 4-14 minutes, NIRT applied | 44.1 | 9.7 | 45.4 | 7.1 |
| 14-18 minutes, no NIRT | 43.9 | 10.9 | 44.3 | 8.3 |

Example 4

Nose clips were constructed by adhering foam to the interior surface of U-shaped pieces of polypropylene which, in the absence of tension, had interior widths of approximately 0.87 inches. Low density polyethylene ("LDPE") foam was laminated to the interior surface of the U-shaped polypropylene, resulting in nose clips that were comfortable to wear. In one instance, a layer of 3/16" LDPE foam was adhered to the interior surface of the U-shaped polypropylene frame. Unlike commercially available nose clips useful for swimming, this nose clip, when worn by adults, did not compress the nose with sufficient force to prevent nasal breathing altogether, even if positioned optimally for that purpose. Instead, the NIRT nose clip was comfortable to wear, and compressed the nose with only a mild force, the extent of which varied according to nose size and placement. Importantly, this compression force, while not excessive, was still sufficient to impede nasal breathing.

Example 5

The force required to obtain internal openings of 1.5 cm and 2.0 cm in various nose clips was measured using a Chatillon Force Gauge Model DPP-2 (which measures up to 2 lb force). Two different commercially available nose clips, which had been worn previously, were compared with the nose clip with 3/16" thick LDPE foam contact points made in Example 4 above. In order to obtain internal openings of 1.5 cm and 2.0 cm, the total deformation of the nose clip from its resting state can come from deformation of the frame of the nose clip (typically metal or plastic), deformation of the elastic materials used in the contact points, or combinations thereof. The experimental results are shown below in Table 3, using an average of ten measurements for each data point.

TABLE 3

| Nose Clip | Force Needed to Obtain 1.5 cm Opening (lb) | Force Needed to Obtain 2.0 cm Opening (lb) |
| --- | --- | --- |
| Speedo Rubber Nose Clip | 0.7 | 1.6 |
| Speedo Competition Nose Clip | 0.7 | 1.4 |
| Example 4 Nose Clip, 3/16" foam | 0.2 | 0.5 |

Example 6

A NIRT nose clip was constructed by adhering round LDPE foam (5/8" diameter) to a U-shaped, coated stainless steel wire backing. The resulting nose clip had an internal opening at the ends, in the absence of any tension, of 1.0 cm (measuring from the parts of the round foam closest to each other). Upon application to a nose, the pressure from this nose clip was distributed in a manner such that the nose clip stayed on the nose easily and was comfortable to wear, and was particularly convenient for use by children.

Incorporation By Reference

All publications, patents, and patent applications cited herein are hereby expressly incorporated by reference in their entirety and for all purposes to the same extent as if each was so individually denoted.

Equivalents

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

The articles "a" and "an" are used herein to refer to one or to more than one (i.e. to at least one) of the grammatical object of the article. By way of example, "a subject" means one subject or more than one subject.

Any ranges cited herein are inclusive, e.g., "between five percent and seventy-five percent" includes percentages of 5% and 75%.

I claim:

1. A method for improving breathing in a human subject, comprising the steps of:
    (A) applying a nasal inspiratory resistance trainer to a human subject's nose such that nasal air flow is inhibited; and
    (B) breathing by the subject for a period of at least five minutes during which the nasal inspiratory resistance trainer is applied to the nose;
    wherein the subject attempts to avoid oral inhalation during said step of breathing;
    wherein said nasal inspiratory resistance trainer inhibits nasal air flow by exerting a compressive force against said human subject's nose; and
    wherein said nasal inspiratory resistance trainer is applied to the nasal cavity such that the initial air flow volume per exhalation is reduced by between about 5% and about 75%.

2. A method for treating a respiratory disorder in a human subject comprising subjecting the subject to multiple training sessions, wherein each training session comprises the steps of:
    (A) applying a nasal inspiratory resistance trainer to the subject's nose which restricts nasal air flow to the subject by exerting a compressive force against the nose; and
    (B) breathing by the subject for a period of at least five minutes during which the nasal inspiratory resistance trainer is applied to the nose;
    wherein the subject attempts to avoid oral inhalation during said step of breathing; and
    wherein the resting $CO_2$ setpoint of said subject increases by at least 3% over the course of treatment.

3. A nasal inspiratory resistance trainer comprising a device that is secured to the nose of a human subject via a compressive force, wherein said compressive force causes the cross-sectional area of the nasal cavity to be reduced, wherein said compressive force is insufficient to prevent nasal inspiration, and wherein said compressive force applied by the nasal inspiratory resistance trainer when the contact points are 1.5 centimeters apart is less than one pound.

* * * * *